US008907149B2

(12) United States Patent
Tirtowidjojo et al.

(10) Patent No.: US 8,907,149 B2
(45) Date of Patent: Dec. 9, 2014

(54) PROCESS FOR THE PRODUCTION OF CHLORINATED PROPENES

(75) Inventors: Max M. Tirtowidjojo, Lake Jackson, TX (US); William J. Kruper, Jr., Sanford, MI (US); Barry B. Fish, Lake Jackson, TX (US); David S. Laitar, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/123,137

(22) PCT Filed: May 18, 2012

(86) PCT No.: PCT/US2012/038759
§ 371 (c)(1),
(2), (4) Date: Nov. 29, 2013

(87) PCT Pub. No.: WO2012/166393
PCT Pub. Date: Dec. 6, 2012

(65) Prior Publication Data
US 2014/0100394 A1    Apr. 10, 2014

Related U.S. Application Data

(60) Provisional application No. 61/491,802, filed on May 31, 2011.

(51) Int. Cl.
*C07C 17/25* (2006.01)
*C07C 17/093* (2006.01)
*C07C 17/10* (2006.01)
*C07C 17/06* (2006.01)
*C07C 17/20* (2006.01)

(52) U.S. Cl.
CPC ............... *C07C 17/06* (2013.01); *C07C 17/10* (2013.01); *C07C 17/25* (2013.01); *C07C 17/202* (2013.01)
USPC .......................................... 570/229; 570/253

(58) Field of Classification Search
CPC ........ C07C 17/25; C07C 17/10; C07C 21/04; C07C 21/21; C07C 19/01; C07C 19/075
USPC .................................. 570/229, 253
See application file for complete search history.

(56) References Cited

U.S. PATENT DOCUMENTS

| 2,119,484 A | 5/1938 | Levine |
| 2,179,378 A | 11/1939 | Metzger |
| 2,299,441 A | 10/1942 | Vaughan |
| 2,302,228 A * | 11/1942 | Kharasch et al. ............ 562/603 |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse |
| 2,688,592 A | 9/1954 | Skeeters |
| 2,762,611 A | 9/1956 | Monroe |
| 2,765,359 A | 10/1956 | Pichler |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl Hans et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A * | 7/1974 | Smith ....................... 570/220 |
| 3,872,664 A | 3/1975 | Lohmann |
| 3,914,167 A | 10/1975 | Ivy |
| 3,926,758 A | 12/1975 | Smith |
| 3,948,858 A | 4/1976 | Wiersum |
| 3,954,410 A | 5/1976 | Pohl |

(Continued)

FOREIGN PATENT DOCUMENTS

| CH | 609022 | 6/1974 |
| CN | 101492341 | 7/2009 |

(Continued)

OTHER PUBLICATIONS

Bai et al, "Isomerization of Tetrachloropropene to Promote Utilization Ratio of Triallate Raw Materials", Petrochemical Technology & Application, 2007, 25(1).
Boualy et al, "Kharasch Addition of Tetrachloromethane to Alkenes Catalyzed by Metal Acetylacetonates", Catalysis Communications, 2011, pp. 1295-1297, vol. 12.
Chai et al., "Study of Preparation of 1,1,1,3-tetrachloropropane", Zhejiang Chemical Industry, 2010, pp. 1-3, 41(5).
Cristiano et al., "Tetraalkylphosphonium Trihalides. Room Temperature Ionic Liquids as Halogenation Reagents", J. Org. Chem., 2009, pp. 9027-9033, vol. 74.
Evstigneev et al., "Initiated Chlorination of Tetrachloropropane", Khim. Prom., 1984, pp. 393-394, 16(7).
Galitzenstein et al., "The Dehydrochlorination of Propylene Dichloride", Journal of the Society of Chemical Industry, 1950, pp. 298-304, vol. 69.

(Continued)

*Primary Examiner* — Jafar Parsa
(74) *Attorney, Agent, or Firm* — Lois K. Ruszala; KSJLAW, LLC (57) ABSTRACT

Processes for the production of chlorinated propenes are provided. The present processes make use of a feedstream comprising 1,2-dichloropropane, a by-product in the production of chlorohydrin, as a low cost starting material, alone or in combination with 1,2,3-trichloropropane. Selectivity of the process is enhanced over conventional processes employing successive chlorinations and/or dehydrochlorinations, by conducting at least one chlorination in the presence of an ionic chlorination catalyst. The present processes may also generate anhydrous HCl as a byproduct that can be removed from the process and used as a feedstock for other processes, providing further time and cost savings.

16 Claims, 2 Drawing Sheets

(56) References Cited

U.S. PATENT DOCUMENTS

| | | | |
|---|---|---|---|
| 4,038,372 A | 7/1977 | Colli | |
| 4,051,182 A * | 9/1977 | Pitt | 562/860 |
| 4,513,154 A | 4/1985 | Kurtz | |
| 4,535,194 A | 8/1985 | Woodard | |
| 4,614,572 A | 9/1986 | Holbrook | |
| 4,644,907 A | 2/1987 | Hunter | |
| 4,650,914 A | 3/1987 | Woodard | |
| 4,661,648 A | 4/1987 | Franklin | |
| 4,702,809 A | 10/1987 | Mueller | |
| 4,714,792 A | 12/1987 | Muller | |
| 4,716,255 A | 12/1987 | Muller | |
| 4,726,686 A | 2/1988 | Wolf | |
| 4,727,181 A | 2/1988 | Kruper | |
| 4,894,205 A | 1/1990 | Westerman | |
| 4,902,393 A | 2/1990 | Muller | |
| 4,999,102 A | 3/1991 | Cox | |
| 5,057,634 A | 10/1991 | Webster | |
| 5,132,473 A | 7/1992 | Furutaka | |
| 5,171,899 A | 12/1992 | Furutaka | |
| 5,178,844 A | 1/1993 | Carter et al. | |
| 5,254,771 A | 10/1993 | Cremer | |
| 5,254,772 A | 10/1993 | Dukat | |
| 5,254,788 A | 10/1993 | Gartside | |
| 5,262,575 A | 11/1993 | Dianis | |
| 5,315,044 A | 5/1994 | Furutaka | |
| 5,414,166 A | 5/1995 | Kim | |
| 5,614,323 A | 3/1997 | Chang | |
| 5,684,219 A | 11/1997 | Boyce | |
| 5,689,020 A | 11/1997 | Boyce | |
| 5,811,605 A | 9/1998 | Tang | |
| 5,895,825 A | 4/1999 | Elsheikh | |
| 5,986,151 A | 11/1999 | Van Der Puy | |
| 6,111,150 A | 8/2000 | Sakyu | |
| 6,118,018 A | 9/2000 | Savidakis | |
| 6,160,187 A | 12/2000 | Strickler | |
| 6,187,976 B1 | 2/2001 | Van Der Puy | |
| 6,229,057 B1 | 5/2001 | Jackson et al. | |
| 6,472,573 B1 | 10/2002 | Yamamoto | |
| 6,538,167 B1 | 3/2003 | Brown | |
| 6,545,176 B1 | 4/2003 | Tsay | |
| 6,551,469 B1 | 4/2003 | Nair | |
| 6,610,177 B2 | 8/2003 | Tsay | |
| 6,683,216 B1 | 1/2004 | Zoeller | |
| 6,825,383 B1 | 11/2004 | Dewkar | |
| 6,958,135 B1 | 10/2005 | Filippi | |
| 7,117,934 B2 | 10/2006 | Lomax | |
| 7,189,884 B2 | 3/2007 | Mukhopadhyay | |
| 7,226,567 B1 | 6/2007 | Olbert | |
| 7,282,120 B2 | 10/2007 | Braun | |
| 7,297,814 B2 | 11/2007 | Yada | |
| 7,345,209 B2 | 3/2008 | Mukhopadhyay | |
| 7,371,904 B2 | 5/2008 | Ma | |
| 7,378,559 B2 | 5/2008 | Verwijs | |
| 7,396,965 B2 | 7/2008 | Mukhopadhyay | |
| 7,511,101 B2 | 3/2009 | Nguyen | |
| 7,521,029 B2 | 4/2009 | Guetlhuber | |
| 7,588,739 B2 | 9/2009 | Sugiyama | |
| 7,659,434 B2 | 2/2010 | Mukhopadhyay | |
| 7,674,939 B2 | 3/2010 | Mukhopadhyay | |
| 7,687,670 B2 | 3/2010 | Nappa | |
| 7,695,695 B2 | 4/2010 | Shin | |
| 7,714,177 B2 | 5/2010 | Mukhopadhyay | |
| 7,836,941 B2 | 11/2010 | Song | |
| 7,880,040 B2 | 2/2011 | Mukhopadhyay | |
| 7,951,982 B2 | 5/2011 | Mukhopadhyay | |
| 8,058,486 B2 | 11/2011 | Merkel | |
| 8,058,490 B2 | 11/2011 | Strebelle | |
| 8,071,825 B2 | 12/2011 | Johnson | |
| 8,071,826 B2 | 12/2011 | Van Der Puy | |
| 8,076,521 B2 | 12/2011 | Elsheikh | |
| 8,084,653 B2 | 12/2011 | Tung | |
| 8,115,038 B2 | 2/2012 | Wilson | |
| 8,123,398 B2 | 2/2012 | Teshima | |
| 8,158,836 B2 | 4/2012 | Pigamo | |
| 8,232,435 B2 | 7/2012 | Sievert | |
| 8,258,353 B2 | 9/2012 | Kruper | |
| 8,258,355 B2 | 9/2012 | Merkel | |
| 8,357,828 B2 | 1/2013 | Okamoto | |
| 8,367,867 B2 | 2/2013 | Zardi | |
| 8,383,867 B2 | 2/2013 | Mukhopadhyay | |
| 8,395,000 B2 | 3/2013 | Mukhopadhyay | |
| 8,487,146 B2 | 7/2013 | Wilson | |
| 8,581,011 B2 | 11/2013 | Tirtowidjojo | |
| 8,581,012 B2 | 11/2013 | Tirtowidjojo et al. | |
| 8,614,361 B2 | 12/2013 | Suzuki | |
| 2001/0018962 A1 | 9/2001 | Joshi | |
| 2002/0110711 A1 | 8/2002 | Boneberg | |
| 2006/0150445 A1 | 7/2006 | Redding | |
| 2006/0292046 A1 | 12/2006 | Fruchey | |
| 2007/0197841 A1 | 8/2007 | Mukhopadhyay | |
| 2007/0265368 A1 | 11/2007 | Rao | |
| 2008/0021229 A1 | 1/2008 | Maughon | |
| 2008/0073063 A1 | 3/2008 | Clavenna et al. | |
| 2008/0118018 A1 | 5/2008 | Schrauwen | |
| 2008/0207962 A1 | 8/2008 | Rao | |
| 2009/0018377 A1 | 1/2009 | Boyce | |
| 2009/0099396 A1 | 4/2009 | Mukhopadhyay | |
| 2009/0117014 A1 | 5/2009 | Carpenter | |
| 2009/0203945 A1 | 8/2009 | Mukhopadhyay | |
| 2010/0041864 A1 | 2/2010 | Kadowaki et al. | |
| 2010/0185029 A1 | 7/2010 | Elsheikh | |
| 2010/0263278 A1 | 10/2010 | Kowoll et al. | |
| 2011/0172472 A1 | 7/2011 | Sakyu | |
| 2011/0218369 A1 | 9/2011 | Elsheikh | |
| 2011/0251425 A1 | 10/2011 | Penzel | |
| 2012/0065434 A1 | 3/2012 | Nose | |
| 2014/0081055 A1 | 3/2014 | Tirtowidjojo | |

FOREIGN PATENT DOCUMENTS

| | | |
|---|---|---|
| CN | 101544535 | 9/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 A2 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| JP | 54-079207 | 6/1979 |
| JP | 2001-151708 | 6/2001 |
| JP | 2001-213820 | 8/2001 |
| JP | 2006-272267 | 10/2006 |
| JP | 2007-021396 | 2/2007 |
| JP | 2008-063314 | 3/2008 |
| JP | 2009-000592 | 1/2009 |
| JP | 2009-046653 | 3/2009 |
| JP | 2011-144148 | 7/2011 |
| LU | 52247 | 12/1966 |
| SU | 899523 | 1/1982 |
| WO | 0138271 | 5/2001 |
| WO | 0138275 | 5/2001 |
| WO | 02059536 A1 | 8/2002 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009/085862 * | 7/2009 |

(56) References Cited

FOREIGN PATENT DOCUMENTS

| WO | 2009087423 | 7/2009 |
|---|---|---|
| WO | 2011060211 | 5/2011 |
| WO | 2011065574 | 6/2011 |
| WO | 2012011844 | 1/2012 |
| WO | 2012081482 | 6/2012 |
| WO | 2012166393 | 12/2012 |

OTHER PUBLICATIONS

Gault et al., "Chlorination of Chloroform", Comptes Rendus Des Seances De L'Academie des Sciences, 1924, pp. 467-469, vol. 179.

Gerding et al., "Raman Spectra of aliphatic chlorine compounds II. Chloroethenes and Chloropropenes", RECUEIL, Jan. 1, 1955, pp. 957-975, vol. 74.

Hatch et al., "Allylic Chlorides. XV. Preparation and Properties of the 1,2,3-Trichloropropenes", JACS, Jan. 5, 1952, pp. 123-126, 74(1).

Hatch et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte der Deutschen Chemischen Gesellschaft, May-Aug. 1893, pp. 1257-1261, 26(2).

Ivanov et al., "Metal Phthalocyanine-Catalyzed Addition of Polychlorine-Containing Organic Compounds to C=C Bonds", Russian Chemical Bulletin, International Edition, Nov. 2009, pp. 2393-2396, 58(11).

Kang et al., "Kinetics of Synthesis of 1,1,1,3,3-pentachlorobutane Catalyzed by Fe-FeCl3", Chemical Research and Application, Jun. 2011, pp. 657-660, 23(6).

Kharasch et al., "Chlorinations with Sulfuryl Chloride. I. The Peroxide-Catalyzed Chlorination of Hydrocarbons", JACS, 1939, pp. 2142-2150, vol. 61.

Khusnutdinov et al., "CCl4 Attachment to Olefins Catalyzed by Chromium and Ruthenium Complexes. Impact of Water as a Nucleophilic Admixture", Oil Chemistry, 2009, pp. 349-356, vol. 4.

Kruper et al., "Synthesis of alpha-Halocinnamate Esters via Solvolytic Rearrangement of Trichloroallyl Alcohols", J. Org. Chem., 1991, pp. 3323-3329, vol. 56.

Leitch, "Organic Deuterium Compounds: V. The chlorination of propyne and propyne D-4", Canadian Journal of Chemistry, Apr. 1, 1953, pp. 385-386, 30(4).

Levanova et al., "Thermocatalytic Reactions of Bromochloropropanes", Russian Journal of Physical Chemistry, Jan. 1, 1983, pp. 1142-1146, vol. 57.

Liu et al., "Progress in the Synthesis of 1,1,1,3-tetrachloropropane", Guangzhou Chemicals, 2011, pp. 41-42, 39(5).

McBee et al., "Utilization of Polychloropropanes and Hexachloroethane", Industrial and Engineering Chemistry, Feb. 1, 1941, pp. 176-181, 33(2).

Mouneyrat, "Effect of Chlorine on Propyl Chloride in the Presence of Anhydrous Aluminum Chloride" Bulletin de la Societe Chimique de Paris, Jan. 1, 1899, pp. 616-623, 3(21).

Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair et al., "Atom Transfer Radical Addition (ATRA) of Carbon Tetrachloride and Chlorinated Esters to Various Olefins Catalyzed by CP'Ru(PPh3)(PR3)Cl Complexes", Inorganica Chimica Acta, 2012, pp. 96-103, vol. 380.

Nikishin et al., "Reactions of Methanol and Ethanol", Seriya Khimicheskaya, Dec. 1966, pp. 2188-2192, vol. 12.

Pozdnev et al., "Chlorination of Chloroform and the Conversion of Methylene Chloride Manufacture Still Residues", Khim., Khim. Tekhnol., 1970, 70(4).

Rotshtein et al., "Isomer Distribution on Chlorination of Chloropropanes", Zhurnal Organicheskoi Khimii, Sep. 1966, pp. 1539-1542, 2(9).

Semenov et al., "Selectivity of Photochemical Chlorination of Chloromethane in the Liquid Phase", Zhurnal Prikladnoi Khimii, Apr. 1985, pp. 840-845, 58(4).

Skell et al., "Reactions of BrCl with Alkyl Radicals", Tetrahedron Letters, 1986, pp. 5181-5184, 27(43).

Skell et al., "Selectivities of pi and sigma-Succinimidyl Radicals in Aubstitution and Addition Reactions. Appendix: Response to Walling, El-Taliawi and Zhao", JACS, Jul. 1, 1983, pp. 5125-5131, 105(15).

Tanuma et al., "Partially Fluorinated Metal Oxide Catalysts for a Friedel-Crafts-type Reaction of Dichlorofluoromethane with Tetrafluoroethylene", Catalysis Letters, 2010, pp. 77-82, vol. 136.

Urry et al., "Free-Radical Reactions of Diazomethane with Reactive Bromopolychloroalkanes", JACS, May 5, 1964, pp. 1815-1819, 86(9).

Wang, "Elimination Reactions of Polyhalopropanes under Emulsion Catalytic Conditions to give Halopropenes", Synthesis, Jun. 1982, pp. 494-496, vol. 6.

Zhao et al, "Research Progress on Preparation Technology of 1,1,2,3-Tetrachloropropene", Zhejiang Chemical Industry, 2010, pp. 8-10, 41(8).

Zheng et al., "Review of the Preparation of the low GWP alternative 1,3,3,3-tetrafluoropropene", Zhejiang Chemical Industry, 2010, pp. 5-7, 41(3).

Fields et al., "Thermal Isomerization of 1,1-dichlorocyclopropanes", Chemical Communications (London) No. 21, Jan. 1, 1967, p. 1081.

Nguyen et al., "Condensation de chloroforme avec des olefins fluourees en milieu basique", Journal of Flourine Chemistry, vol. 55, No. 3, Dec. 1, 1991, pp. 241-248.

Shelton et al., "Addition of Halogens and Halogen Compounds to Allylic Chlorides. I. Addition of Hydrogen Halides," Journal of Organic Chemistry, 23, pp. 1876-1880 (1958).

Tobey et al., Pentachlorocyclopropane 1, Journal of the American Chemical Society, vol. 88, No. 11, Jun. 1, 1996, pp. 2478-2481.

* cited by examiner

PROCESS FOR THE PRODUCTION OF CHLORINATED PROPENES

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost. This may be due at least in part to the fact that conventional processes for their manufacture may require the use of starting materials that are prohibitively expensive to be economically produced by manufacturers on the large scale required to be useful as feedstocks. Additionally, conventional processes may require multiple chlorination and dehydrochlorination steps to arrive at a desired level of chlorination in the final product. Dehydrochlorination steps are typically conducted with an aqueous base, and result in the production of large quantities of waste water containing large quantities of sodium chloride and/or chlorinated organics. Treatment of this waste water is time consuming and expensive, and results in the recovery of low value by-products.

It would thus be desirable to provide improved processes for the large capacity and/or continuous production of chlorocarbon precursors useful as feedstocks in the synthesis of refrigerants and other commercial products. More particularly, such processes would provide an improvement over the current state of the art if they were less costly in starting materials, processing time, and/or capital costs required to implement and maintain the process. Generation of byproducts having a higher value than sodium chloride, or really any value, would be a further advantage if provided in such a process.

BRIEF DESCRIPTION

The present invention provides efficient processes for the production of chlorinated propenes. Advantageously, the processes make use of 1,2-dichloropropane, a by-product in the production of chlorohydrin, as a low cost starting material, alone or in combination with 1,2,3-trichloropropane. Selectivity of the process is enhanced over conventional chlorination processes by employing successive chlorination steps, using an ionic chlorination catalyst, and dehydrochlorination steps. Because 1,2-dichloropropane and 1,2,3-trichloropropane are directly chlorinated to chlorinated propene isomers, fewer steps are required than conventional processes, and capital cost and time savings are provided. Further, since lesser amounts of chlorinated propane intermediates are processed through caustic cracking, anhydrous HCl can be recovered from the process rather than the lower value NaCl produced by multiple caustic cracking steps. Less waste water is thus generated, providing further time and cost savings.

In one aspect, the present invention provides a process for the production of chlorinated propenes from one or more chlorinated alkanes. The process comprises at least one liquid phase chlorination step conducted in the presence of an ionic chlorination catalyst and at least one dehydrochlorination step. The one or more chlorinated alkanes comprise 1,2-dichloropropane, and may further comprise 1,2,3-trichloropropane. The chlorination agent comprises chlorine, sulfuryl chloride ($SO_2Cl_2$), or combinations of these. The ionic chlorination catalyst desirably comprises aluminum chloride ($AlCl_3$), iodine ($I_2$), ferric chloride ($FeCl_3$) and other iron containing compounds, iodine, sulfur, antimony pentachloride ($SbCl_5$), boron trichloride ($BCl_3$), lanthanum halides, metal triflates, or combinations of these. The chlorinated propene produced desirably comprises from 3 to 5 chlorine atoms, and in some embodiments, may be 1,1,2,3-tetrachloropropene. HCl is generated by the process as a by-product, and in some embodiments, may be recovered in its anhydrous form for use, e.g., in downstream processes. Further, one or more reactants may be generated within or upstream of the process.

The advantages provided by the present processes may be carried forward by utilizing the chlorinated and/or fluorinated propenes to produce further downstream products, such as, e.g., 2,3,3,3-tetrafluoroprop-1-ene or 1,3,3,3-tetrafluoroprop-1-ene.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "PDC" may be used as an abbreviation for 1,2-dichloropropane, "TCP" may be used as an abbreviation for 1,2,3-trichloropropane and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of a hydrogen and a chlorine atom from adjacent carbon atoms in chlorinated hydrocarbon reagents.

The present invention provides efficient processes for the production of chlorinated propenes. The present processes comprise conducting successive ionic chlorination and dehydrochlorination steps on one or more chlorinated alkanes comprising PDC. Catalysts are used during one or more of the chlorination steps that promote highly selective ionic chlorination. The use of PDC, a byproduct in many chlorohydrin processes, as a starting material is economically more attractive than disposing of it via incineration, as may be done in connection with some conventional chlorohydrin processes.

The present process is further advantageous since a saleable product can be reached in fewer steps, resulting in lower capital costs as compared to conventional processes. More specifically, the fact that the present processes are conducted in the liquid phase, using free radical chlorination, is advantageous compared to conventional methods for producing chlorinated propenes using gas-phase thermal chlorination reactions because the production utility cost is lower for a process comprising liquid phase reactions, where evaporation of reactants is not required. In addition, the lower reaction temperatures used in the present liquid phase reactions tend to result in lower fouling rates than the higher temperatures used in connection with gas phase reactions. Higher fouling rates, in turn, tend to limit reactor lifetime and can lead to undesirable byproduct formation.

The present processes, in some embodiments, may also provide a reduction of caustic cracking steps as compared to conventional processes, and so, anhydrous HCl can be recovered. Anhydrous HCl is of greater value than the sodium chloride that would be produced as byproducts) if conventional caustic cracking steps were utilized. And so, the present process results in the production of a by-product that may either be sold or used as a feedstock for other processes, e.g., ethylene oxychlorination to produce ethylene dichloride.

The present process makes use of one or more chlorinated alkanes to produce the desired chlorinated propenes. Desirably, the one or more chlorinated alkanes comprise 1,2-dichloropropane, which may be available at low cost due to its production as a by-product in many chlorohydrin processes. The process feedstock may also comprise trichloropropane, or other chlorinated alkanes, if desired. And, the one or more chlorinated alkanes may be generated within or upstream of the process, if desired, e.g., as a byproduct in a chlorohydrin process, or by any other methods known to those of ordinary skill in the art.

Any chlorinated propene may be produced using the present method, although those with 3-5 chlorine atoms are more commercially sought after, and production of the same may thus be preferred in some embodiments. In some embodiments, the process may be used in the production of 1,1,2,3-tetrachloropropene, which is highly sought after as a feedstock for refrigerants, polymers, biocides, etc.

The use of ionic chlorination catalysts in the present process is particularly advantageous since they dehydrochlorinate and chlorinate alkanes at the same time. That is, ionic chlorination catalysts remove a chlorine and hydrogen from adjacent carbon atoms, the adjacent carbon atoms form a double bond, and HCl is released. A chlorine is then added back, replacing the double bond, to provide a more highly chlorinated alkane.

Ionic chlorination catalysts are well known to those or ordinary art and any of these may be used in the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof.

In some embodiments, the dehydrochlorination steps of the present process may be carried out in the presence of a catalyst so that the reaction rate is enhanced and also use of liquid caustic is reduced, or even eliminated, from the process. Such embodiments are further advantageous in that anhydrous HCl is produced, which is a higher value byproduct than aqueous HCl. If the use of catalysts is desired, suitable dehydrochlorination catalysts include, but are not limited to, ferric chloride ($FeCl_3$) as a substitute to caustic.

In other embodiments, one or more of the dehydrochlorination steps of the present process may be conducted in the presence of a liquid caustic. Although vapor phase dehydrochlorinations advantageously result in the formation of a higher value byproduct than liquid phase dehydrochlorinations, liquid phase dehydrochlorination reactions can provide cost savings since evaporation of reactants is not required. The lower reaction temperatures used in liquid phase reactions may also result in lower fouling rates than the higher temperatures used in connection with gas phase reactions, and so reactor lifetimes may also be optimized when at least one liquid phase dehydrochlorination is utilized.

Many chemical bases are known in the art to be useful for liquid dehydrochlorinations, and any of these can be used. For example, suitable bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts (e.g. benzyltrimethylammonium chloride or hexadecyltributylphosphonium bromide) can also be added to improve the dehydrohalogenation reaction rate with these chemical bases.

Any or all of the catalysts utilized in the process can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate format and method of introduction thereof. For example, many catalysts are typically introduced into the reactor zone as a separate feed, or in solution with other reactants.

The amount of any ionic chlorination and/or dehydrochlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only then, it is expected, that useful concentrations of the ionic chlorination catalyst will range from 0.001% to 20% by weight, or from 0.01% to 10%, or from 0.1% to 5 wt. %, inclusive of all subranges therebetween. If a dehydrochlorination catalyst is utilized for one or more dechyrdochlorination steps, useful concentrations may range from 0.01 wt. % to 5 wt. %, or from 0.05 wt. % to 2 wt. % at temperatures of from 70° C. to 200° C. If a chemical base is utilized for one or more dehydrochlorinations, useful concentrations of these will range from 0.01 to 20 grmole/L, or from 0.1 grmole/L to 15 grmole/L, or from 1 grmole/L to 10 grmole/L, inclusive of all subranges therebetween. Relative concentrations of each catalyst/base are given relative to the feed, e.g., 1,2-dichloropropane alone or in combination with 1,2,3-trichloropropane.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, etc.

That being said, the particular conditions employed at each step described herein are not critical, and are readily determined by those of ordinary skill in the art. What is important is that a feedstream comprising 1,2-dichloropropane, either alone or in combination with 1,2,3-trichloropropane, is used as a starting material, and/or an ionic chlorination catalyst is utilized and/or that provisions are made for the recovery of anhydrous HCl. Those of ordinary skill in the art will readily be able to determine suitable equipment for each step, as well as the particular conditions at which the chlorination, dehydrochlorination, separation, drying, and isomerization steps may be conducted.

In the present process, a feed stream comprising fresh 1,2-dichloropropane, either alone, or in some embodiments, in combination with 1,2,3-trichloropropane is converted to TCPE using at least one chlorination step conducted in the presence of an ionic chlorination catalyst.

In one exemplary embodiment, PDC is fed to a liquid phase reactor, e.g., such as a batch or continuous stirred tank autoclave reactor with an internal cooling coil. A shell and multitube exchanger followed by vapor liquid disengagement tank or vessel can also be used. Suitable reaction conditions include, e.g., temperatures of from ambient temperature (e.g., 20° C.) to 200° C., or from 30° C. to 150° C., or from 40° C. to 120° C. or from 50° C. to 100° C. Ambient pressure may be used, or pressures of from 100 kPa to 1000 kPa, or from 100 kPa to 500 kPa, or from 100 kPa to 300 kPa. At such conditions, and using one or more ionic chlorination catalysts, PDC is chlorinated to tri-, tetra-, and pentachlorinated propanes at conversions of greater than 60%, or 70%, or 80%, or 85%, or 90% or 95%, or even up to 100% can be seen.

The process may be carried out neat, i.e., in the absence of solvent, or, one or more solvents may be provided to the chlorination reactor, and may be provided as feedstock, or, recycled from one or more separation columns operably disposed to receive streams from the chlorination reactor. For example, monochloropropene intermediates may be recycled back to the chlorination reactor from one separation column, tri- and tetrachloropropane intermediates may be recycled from another separation column and/or the chlorination reactor may be provided with a feedstock of any appropriate solvent for chlorination reactions, such as, e.g., carbon tetrachloride, sulfuryl chloride, 1,1,2,3,3-pentachloropropane, 1,1,2,2,3,3-hexachloropropane, other hexachloropropane isomers, or other suitable aqueous or alcohol based solvents, or a combination of these.

The overhead vapor from the chlorination reactor, is cooled, condensed and fed to a first separation column. This column is operated at conditions effective to provide anhydrous HCl to an overhead line thereof and chlorine through a bottom recycle line.

More particularly, the top temperature of such a column can typically be set below 0° C. or more preferably, can be set at a temperature of from −70° C. to −10° C. The bottom temperature of this column is desirably set at from 10° C. to 150° C., or from 30° C. to 100° C., with the exact temperature dependent to some degree on the bottom mixture composition. The pressure of this column is desirably set above 200 kPa or preferably, from 500 kPA to 2000 kPa, or more preferably from 500 kPa to 1000 kPa. The bottom stream of a column operated at such conditions would be expected to contain excess chlorine, unreacted PDC and monochloropropene intermediates, while the overhead stream would be expected to comprise anhydrous HCl.

The liquid product stream from the chlorination reactor may be fed to a second separation column operated at conditions effective to separate the tri- and tetra-chlorinated propanes from the pentachlorinated propanes. The overhead stream from this separation column, comprising tri- and tetra-chlorinated propanes, may be recycled back to the chlorination reactor for further conversion/chlorination, while the bottom stream, expected to comprise pentachloropropanes and heavier by-products, such as isomers of hexachloropropanes, may be provided to a further separation column.

This third separation column separates the desirable pentachloropropanes, i.e., 1,1,2,2,3-pentachloropropane, 1,1,1, 2,3-pentachloropropane, and 1,1,1,2,2-pentachloropropane, from the less desirable 1,1,2,3,3-pentachloropropane and heavier components, which are purged as a bottom stream.

The overhead stream comprising 1,1,2,2,3-pentachloropropane, 1,1,1,2,3-pentachloropropane, and 1,1,1,2,2-pentachloropropane is then provided to a reactor where it is dehydrochlorinated to provide 2,3,3,3-tetrachloropropene and 1,1,2,3-tetrachloropropene. More specifically, dehydrochlorination reactor may typically be a batch or a continuous stirred tank reactor. The mixing can be done, e.g., by mechanical or jet mixing of feed streams. Those of ordinary skill in the art are readily able to determine the appropriate conditions at which to run a dehydrochlorination reactor in order to conduct the aforementioned dehydrochlorination.

The reaction stream from the dehydrochlorination reactor may optionally be provided to a drying column, and the dried stream therefrom provided to a further reactor to isomerize the 2,3,3,3-tetrachloropropene to 1,1,2,3-tetrachloropropene under the appropriate conditions. For example, catalysts may be utilized to assist in the isomerization, in which case, suitable catalysts include, but are not limited to (i) siliceous granules having a polar surface including kaolinite, bentonite, and attapulgite; (ii) other mineral salts of silica such as saponite, quartz, (iii) siliceous non-mineral substance such as silica gel, fumed silica, and glass, or combinations of any of these. Suitable conditions for drying columns for such reaction streams are also known to those of ordinary skill in the art, as evidenced by U.S. Pat. No. 3,926,758.

Figure 1:
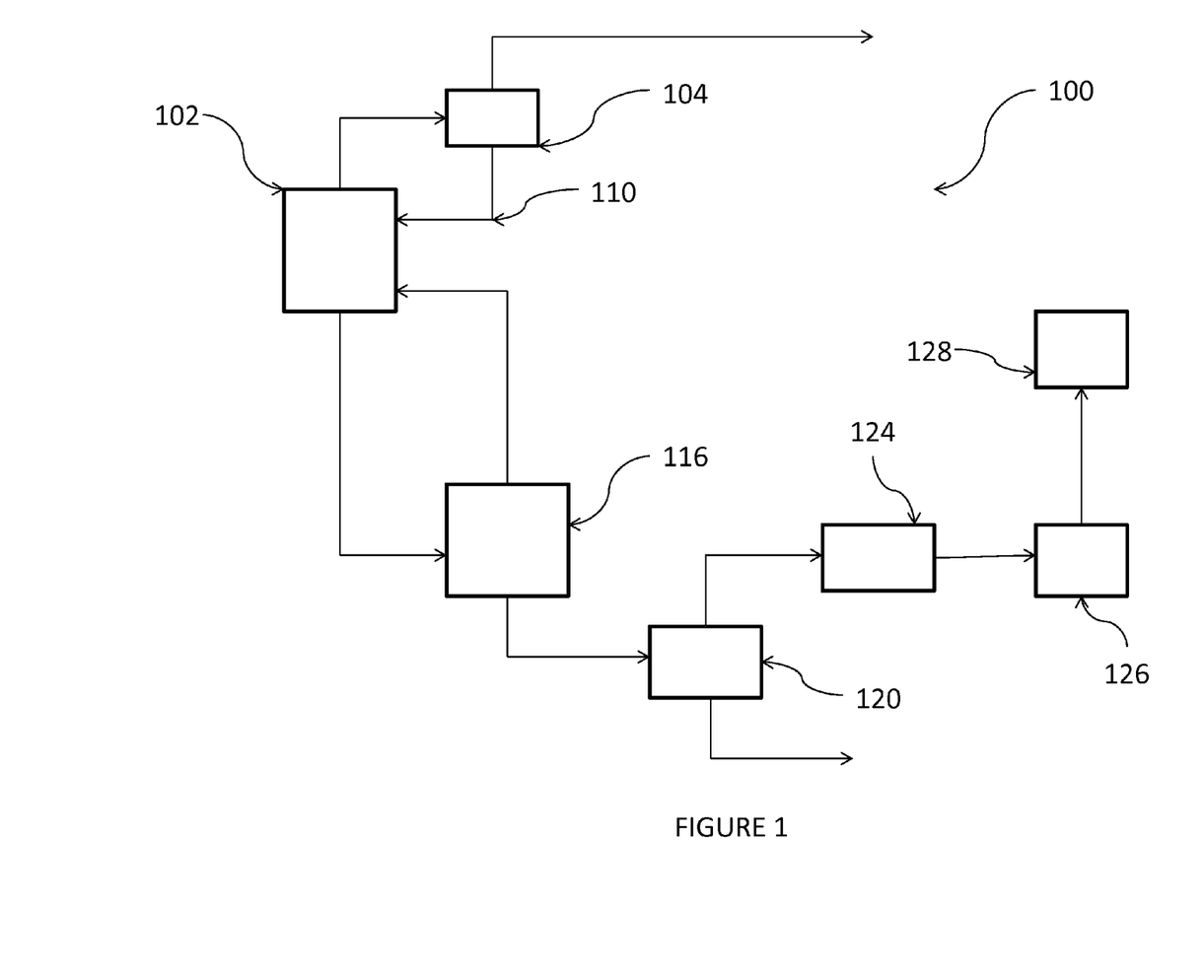
FIG. 1 shows a schematic representation of a process according to one embodiment.

A schematic illustration of such a process is shown in FIG. 1. As shown in FIG. 1, process 100 would make use of chlorination reactor 102, separation columns 104, 116 and 120, dehydrochlorination reactor 124, dryer 126 and isomerization reactor 128. In operation, 1,2-dichloropropane (alone or in combination with trichloropropane), one or more ionic chlorination catalysts and the desired chlorination agent (e.g., chlorine, $SO_2Cl_2$, or combinations of these) are fed, or otherwise provided, to chlorination reactor 102, which may be operated at any set of conditions operable to provide for the chlorination of PDC to tri-, tetra- and pentachlorinated propanes.

The overhead stream of chlorination reactor 102 is fed to separation column 104. The feed to the separation column is preferably totally condensed liquid at temperature −40° C. to 0° C. made by applying a fractionation method such as that described in U.S. Pat. No. 4,010,017.

Separation column 104 is operated at conditions effective to provide anhydrous HCl through an overhead line and chlorine, PDC, and monochloropropene intermediates back to chlorination reactor 102. The bottom stream of reactor 102 is fed to separation column 116, which is operated at conditions effective to separate the tri- and tetra-chlorinated propanes from the pentachlorinated propanes. The tri- and tetra chlorinated propanes are recycled back to chlorination reactor 102 for further conversion/chlorination, while the bottom stream from separation column is fed to separation column 120.

Separation column 120 separates the bottom stream from column 116 into an overhead stream comprising the desirable pentachloropropane isomers (1,1,1,2,2-pentachloropropane, 1,1,2,2,3-pentachloropropane and 1,1,1,2,3-pentachloropropane) and a bottom stream comprising the less desirable 1,1,2,3,3-pentachloropropane, hexachloropropane and heavier by-products. The overhead stream is fed to dehydrochlorination reactor 124, while the bottoms stream is appropriately disposed of.

Within dehydrochlorination reactor 124, the desirable pentachloropropane isomers are dehydrochlorinated to provide 2,3,3,3-tetrachloropropene and 1,1,2,3-tetrachloropropene. More specifically, dehydrochlorination reactor 124 may be charged with, e.g., a dehydrochlorination catalyst or caustic and operated at pressures of from ambient to 400 kPA, and at temperatures of 40° C. to 150° C. and at residence times of less than 3 hours. The reaction stream from dehydrochlorination reactor 124 is fed to drying column 126, and the dried stream therefrom provided to isomerization reactor 128 to isomerize the 2,3,3,3-tetrachloropropene to 1,1,2,3-tetrachloropropene under the appropriate conditions.

Figure 2:
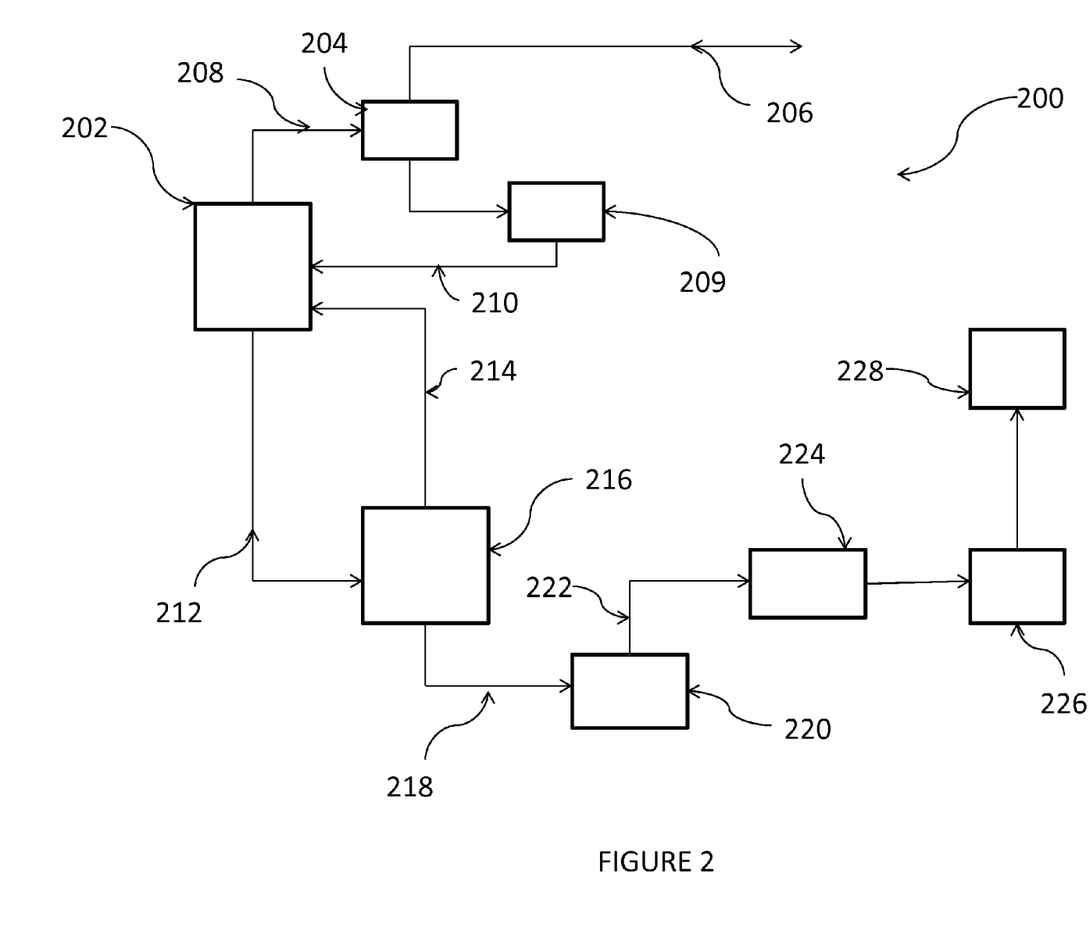
FIG. 2 shows a schematic representation of a process according to a further embodiment.

One further exemplary process for the production of chlorinated propenes is schematically illustrated in FIG. 2. Process 200 is similar to process 100, except that $SO_2Cl_2$ is used in place of $Cl_2$ in chlorination reactor 202. And so, the overhead stream from chlorination reactor 202 comprises, HCl, PDC, $Cl_2$ and $SO_2$. Separation column 204 receives this stream via line 208, and separates anhydrous HCl therefrom, which is then discharged via overhead line 206. The bottom stream from separation column 204 is fed to reactor 209. In reactor 209, monochloropropene intermediates and $SO_2$ react with added fresh $Cl_2$ to produce trichloropropanes and $SO_2Cl_2$, respectively, which are recycled back to reactor 202 via line 210. The use of $SO_2Cl_2$ is beneficial since $SO_2Cl_2$ is more miscible with PDC with or without TCP in chlorination reactor 202, thus possibly providing better process yield and productivity. Process 200 is otherwise identical to process 100, shown in FIG. 1.

The chlorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated propenes to provide hydrofluoroolefins may broadly comprise a single reaction or two or more reactions involving fluorination of a compound of the formula $C(X)_m CCl(Y)_n (C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of a chlorinated propene is fluorinated in a catalyzed, gas phase reaction to form a compound such as 1-chloro-3,3,3-trifluoropropene (1233zd). The 1-chloro-2,3,3,3-tetrafluoropropane is then dehydrochlorinated to 2,3,3,3-tetrafluoroprop-1-ene or 1,3,3,3-tetrafluoroprop-1-ene via a catalyzed, gas phase reaction.

EXAMPLE I

Chlorination of 0.95 gr of PDC to 1,1,2,2,3-pentachloropropane (240aa) is conducted with 4.5 molar equivalent of $SO_2Cl_2$ for 8 hours at from 50° C. to 70° C. A 4 dram vial equipped with micro-flea stir bar and water condenser at the overhead padded with $N_2$ is used. The combined catalysts (7 mg $I_2$, 20 mg $AlCl_3$) are added to the solvent under $N_2$ and the reaction is heated to 55° C. for 3 hours. The loss of HCl and $SO_2$ decreased over this period and so the reaction is heated to reflux (70° C. headspace) for 4 hours while monitoring by NMR. At 7 hours another 1 equivalent of $SO_2Cl_2$ (1.13 g) is added and reflux is continued for 1 more hour. The reaction content is then added to 5 mL cold water with mixing to give a clear white phase of oil. The bottom phase is carefully pipetted and the aqueous phase extracted with 4 mL of CH$_2$Cl$_2$. The combined organic phase is dried over MgSO$_4$ and evaporated to give 1.55 g (estimated 89% theoretical recovery) of a 4:1 ratio of mainly 1,1,2,2,3-PCP to 1,2,3-TCP.

The product distribution after the first 7 hours of reaction with a 3.5 molar ratio of SO$_2$Cl$_2$ to PDC is show in Table 1. The absence of 1,1,2,3,3-pentachloropropane (11233) is highly desirable as dehydrochlorination of the same can result in undesirable TCPE isomers (cis/trans-1,2,3,3-tetrachloropropenes and/or 1,1,3,3-tetrachloropropenes). On the other hand, dehydrochlorination of 1,1,2,2,3-pentachloropropane will result in either TCPE or 2,3,3,3-tetrachloropropene that is readily be isomerized to TCPE (See, e.g., U.S. Pat. No. 3,823,195). Dehydrochlorination of 1,1,1,2,2-pentatchloropropane results in desirable intermediate 2,3,3,3-tetrachloropropene. About 4.24% of the product is a mixture of hexachloropropanes, a waste intermediate. This amount can be minimized by adjusting the ratio of catalyst to reactant (i.e., SO$_2$Cl$_2$/PDC), reaction time, and/or temperature. The tri- and tetrachlorinated propane intermediates can also be recycled to improve the process yield.

TABLE 1

| | |
|---|---|
| 1,1,2,2,3-pentachloropropane | 53.05% |
| 1,1,2,3,3-pentachloropropane | 0.00% |
| 1,1,1,2,2-pentachloropropane | 1.33% |
| 1,1,1,2,3-pentachloropropane | 0.00% |
| 1,1,2,2-tetrachloropropane | 1.06% |
| 1,1,2,3-tetrachloropropane | 3.18% |
| 1,2,2,3-tetrachloropropane | 5.84% |
| 1,1,1,2-tetrachloropropane | 0.00% |
| 1,1,2-trichloropropane | 12.20% |
| 1,2,2-trichloropropane | 0.00 |
| 1,2,3-trichloropropane | 19.10% |
| Hexachloropropane isomers | 4.24% |

The product composition of further chlorination of the reaction mixture shown in Table 1 using an additional 1 equimolar of SO$_2$Cl$_2$ is listed in Table 2. These results show that further chlorination of tri- and tetra-chlorinated propane intermediates leads to the desired 1,1,2,2,3-pentachloropropane and 1,1,1,2,2-pentachloropropane without substantial, or any, formation of 1,1,2,3,3-pentachloropropane.

TABLE 2

| | |
|---|---|
| 1,1,2,2,3-pentachloropropane | 66.36% |
| 1,1,2,3,3-pentachloropropane | 0.00% |
| 1,1,1,2,2-pentachloropropane | 0.46% |
| 1,1,1,2,3-pentachloropropane | 0.00% |
| 1,1,2,2-tetrachloropropane | 0.00% |
| 1,1,2,3-tetrachloropropane | 3.94% |
| 1,2,2,3-tetrachloropropane | 0.99% |
| 1,1,1,2-tetrachloropropane | 0.00% |
| 1,1,2-trichloropropane | 1.31% |
| 1,2,2-trichloropropane | 0.00% |
| 1,2,3-trichloropropane | 18.4% |
| Hexachloropropane isomers | 8.54% |

EXAMPLE II

This example may be carried out according to the process shown in FIG. 1.

In reactor 102, PDC is chlorinated in the liquid phase together with recycled trichloropropanes (C$_3$H$_5$Cl$_3$), tetrachloropropanes (C$_3$H$_4$Cl$_4$) and monochloropropenes in the presence of from 1 wt. % to 5 wt. % of AlCl$_3$ and 0.5-2 wt. % of I$_2$, based upon the weight percent of PDC, at a temperature of from 50° C. to 70° C., and a pressure of 200 kPa. The overhead vapor from the reactor is condensed at a temperature of from −40° C. to −10° C. and the condensed liquid fed to separation column 104 set at a pressure of from 500 kPa to 1000 kPa to recover excess Cl$_2$, PDC, monochloropropene, and HCl. The purified anhydrous HCl is taken as an overhead stream from separation column 104, while the bottom stream, comprising Cl$_2$, PDC, and monochloropropene intermediates, is recycled back to chlorination reactor 102.

The liquid product stream from the chlorination reactor 102 is fed to a separation column 116, operating at lower than 50 kPa with a reboiler temperature of 95° C. or lower, that separates the trichloropropanes and tetrachloropropanes from the product stream and recycles them back to the chlorination reactor 102. The bottom stream from separation column 116 contains pentachloropropanes (PCP) and heavier byproducts and is fed to a further separation column 120. In this column, the desirable pentachloropropane isomers are purified from the less desirable 1,1,2,3,3-pentachloropropane isomer and heavier components that purged in via the bottom stream of this column. This column is also operated below 50 kPa to minimize reboiler temperature to below 120° C.

The purified pentachloropropane overhead stream from this separation column (122), comprising 1,1,1,2,3-pentachloropropene and 1,1,2,2,3-pentachloropropane, is caustic cracked to 2333 TCPE and TCPE in a cracking reactor (124) using 2 to 5 grmole/L caustic at a temperature of from 60° C.-90° C. After drying (126), the TCPE and 2333 are isomerized (in reactor 128) to the desired TCPE product using clay granule or silica fixed bed reactor operated at a pressure of from 100 kPa to 150 kPa with 40 minutes residence time or less.

EXAMPLE III

A 50 mL flask is charged with 49 g SO$_2$Cl$_2$ and 1.9 g AlCl$_3$ before heating to 60° C. Once so heated, the reactor is charged with 4.1 g PDC and allowed to react for 24 hours. The crude product mixture is analyzed by gas chromatography and found to be 77.2% 1,1,2,2,3-pentachloropropane, 9.2% hexachloropropanes, 4.5% tetrachloropropanes, and 4.5% residual trichloropropanes.

The crude product mixture is diluted with methylene chloride and charged to a reactor with 2.4 equivalents of aqueous sodium hydroxide. The solution is heated to 42° C. and held for 23 hours. The crude product mixture is analyzed by GC to show that 9% conversion of 1,1,2,2,3-pentachloropropane to the 1,1,2,3-tetrachloropropene is achieved at this low temperature. The remainder of the chloropropane impurities remained unchanged over the course of the caustic cracking procedure.

EXAMPLE IV

Chlorine is passed (30% v/v in N$_2$) at ~200 sccm through a mixture of PDC (57.80 gr) and FeCl$_3$ (1 gr), at 100° C. for 5 hours at a reactor pressure of ~125 psig. The crude product mixture is quenched with aqueous sodium bicarbonate. Analysis by NMR spectroscopy indicated complete consumption of the PDC and the product composition shown in Table 3. This example shows that PDC may be directly chlorinated to trichloropropanes with high selectivity, specifically to 1,1,2-trichloropropane and 1,2,3-trichloropropane at PDC conversion higher than 80% with byproduct (e.g., 1,1,2,3-tetra and 1,1,2,2,3-pentachloropropane) selectivity of less than 10%.

TABLE 3

| | |
|---|---|
| 1,1,2,2,3-pentachloropropane | 3.1% |
| 1,1,2,3,3-pentachloropropane | 0.0% |
| 1,1,1,2,2-pentachloropropane | 0.4% |
| 1,1,1,2,3-pentachloropropane | 0.0% |
| 1,1,2,2-tetrachloropropane | 0.3% |
| 1,1,2,3-tetrachloropropane | 3.1% |
| 1,1,1,2-tetrachloropropane | 0.0% |
| 1,1,2-trichloropropane | 71.2% |
| 1,2,2-trichloropropane | 0.0% |
| 1,2,3-trichloropropane | 19.2% |
| Hexachloropropane isomers | 2.3% |

EXAMPLE V

Chlorination of PDC to a mixture containing 1,1,2,2,3-pentachloropropane (240aa) is achieved by passing $Cl_2$ (30% v/v in $N_2$) at ~100 sccm through a mixture of PDC (11.56 gr), $AlCl_3$ (0.170 gr), $SbCl_5$ (0.381 gr) and $CH_2Cl_2$ (37.2 mL) at 70° C. for 6.75 hours at a reactor pressure of ~100 psig. The crude product mixture is quenched with aq. $NaHCO_3$. Analysis by NMR spectroscopy indicated complete consumption of the PDC and the product composition shown in Table 3. This example shows that PDC may be directly chlorinated to 1,1,2-trichloropropane with high selectivity, and may also provide 1,2,3-trichloropropane, 1,1,2,3-tetra and 1,1,2,2,3-pentachloropropanes with low production of hexachloropropanes.

TABLE 4

| | |
|---|---|
| 1,1,2,2,3-pentachloropropane | 13.4% |
| 1,1,2,3,3-pentachloropropane | 0.0% |
| 1,1,1,2,2-pentachloropropane | 0.3% |
| 1,1,1,2,3-pentachloropropane | 0.0% |
| 1,1,2,2-tetrachloropropane | 0.6% |
| 1,1,2,3-tetrachloropropane | 2.9% |
| 1,1,1,2-tetrachloropropane | 0.00% |
| 1,1,2-trichloropropane | 64.9% |
| 1,2,2-trichloropropane | 0.00 |
| 1,2,3-trichloropropane | 10.6% |
| Hexachloropropane isomers | 7.3% |

EXAMPLE V

The conversion of PDC to trichloropropane isomers was achieved by charging 0.3 g $FeCl_3$ and 51 g $SO_2Cl_2$ to a 50 mL flask prior to heating to 60° C. The reaction was then charged with 9.5 g PDC. After 8 hours, a sample aliquot was analyzed by GC to show that the reaction mixture consisted of 79% starting material, 7.1% 1,1,2-trichloropropane, 6.2% 1,2,3-trichloropropane, 2.5% 1,1,2,2,-tetrachloropropane, 1.2% 1,2,2,3-tetrachloropropane, and 0.2% 1,1,2,3-tetrachloropropane. This mixture could be further utilized for the production of chloropropenes as detailed in the above examples.

The invention claimed is:

1. A process for the production of chlorinated propenes from one or more chlorinated alkanes comprising 1,2-dichloropropane, comprising a chlorination step, conducted in the presence of an ionic chlorination catalyst, and a dehydrochlorination step, wherein the chlorinated propene comprises from 3 to 5 chlorine atoms.

2. The process of claim 1, wherein the one or more chlorinated alkanes further comprise 1,2,3-trichloropropane.

3. The process of claim 1 or 2, wherein the chlorination step produces a mixture of trichloropropane, tetrachloropropane, and pentachloropropane.

4. The process of claim 3, wherein the mixture of trichloropropane, tetrachloropropane and pentachloropropane is dehydrochlorinated in the presence of a dehydrochlorinating catalyst.

5. The process of claim 1, wherein the ionic chlorination catalyst comprises $AlCl_3$, $I_2$, $FeCl_3$, sulphur, iron, antimony pentachloride, boron trichloride, one or more lanthanum halides, one or more metal triflates, or combinations of these.

6. The process of claim 1, wherein the chlorinated propene comprises 1,1,2,3-tetrachloropropene.

7. The process of claim 4, wherein the dehydrochlorination is conducted in the liquid phase.

8. The process of claim 4, wherein the dehydrochlorination is conducted in the gas phase.

9. The process of claim 1, further comprising the use of $Cl_2$, $SO_2Cl_2$ or combinations of these as a chlorinating agent.

10. The process of claim 1, wherein HCl is generated as a byproduct and recovered as anhydrous HCl.

11. The process of claim 1, wherein a per pass conversion of 1,2-dichloropropane is greater than or equal to 50%.

12. The process of claim 11, wherein trichloropropane and tetrachloropropane intermediate byproducts are recycled to the 1,2-dichloropropane chlorination reactor.

13. The process of claim 12, wherein trichloropropane and/or tetrachloropropane are purified together and chlorinated separately from 1,2-dichloropropane.

14. A process for preparing 2,3,3,3-tetrafluoroprop-1-ene or 1,3,3,3-tetrafluoroprop-1-ene comprising converting a chlorinated propene according to claim 1, into 2,3,3,3-tetrafluoroprop-1-ene or 1,3,3,3-tetrafluoroprop-1-ene.

15. The process of claim 1, wherein a feedstream to the process is provided from an upstream chlorohydrin process.

16. The process of claim 4, wherein the dehydrochlorination catalyst comprises ferric chloride.

\* \* \* \* \*